United States Patent [19]

Blanchard et al.

[11] 4,448,779

[45] May 15, 1984

[54] USE OF MS SALT IN GERIATRIC MEDICINE

[75] Inventors: Jean F. Blanchard; Pierre P. Lasserre, both of Toulouse, France

[73] Assignee: Sanofi, Paris, France

[21] Appl. No.: 283,829

[22] Filed: Jul. 16, 1981

[51] Int. Cl.³ ............................................. A61K 31/44
[52] U.S. Cl. .................................................... 424/263
[58] Field of Search ................................ 424/256, 263

[56] References Cited

U.S. PATENT DOCUMENTS 4,097,482 6/1978 Anselem ............................... 424/256
4,147,787 4/1979 Maffrand .............................. 424/256

Primary Examiner—Stanley J. Friedman
Attorney, Agent, or Firm—Weiser, Stapler & Kimmelman

[57] ABSTRACT

Administration of the known drug 5-o-cyanobenzyl-4,5,6,7-tetrahydrothieno [3,2-c] pyridine methanesulfonate ("MS salt" or "PCR") is described for the alleviation of the symptoms of senility such as of organic brain syndrome and senile dementia.

16 Claims, No Drawings

USE OF MS SALT IN GERIATRIC MEDICINE

BACKGROUND OF THE INVENTION

The present invention relates to geriatric medicine and, more particularly, to the treatment of senile organic grain syndrome (OBS) by the use of the known drug, 5-o-cyanobenzyl-4,5,6,7-tetrahydrothieno [3,2-c] pyridine methanesulfonate (MS salt).

The phenomenal advances in medicine both therapeutic and preventive, during the past 40 years have significantly increased longevity. This increase in life span, unfortunately, does not necessarily mean that the increasing numbers of elderly people are able to retain a functionally useful and self-supporting capacity during their added years of life. At present there is no drug which is capable of reversing the aging process, it is not likely that such a drug will be discovered in the forseeable future.

Moreover, the central nervous system is particularly susceptible to early or premature senile deterioration. The term aging in itself has little or no pathological significance. Aging is a continuous process which proceeds all the way through life. Senile deterioration is so common and gradual that it could be considered as being a normal condition. It appears that for the great majority of individuals this is a progressive and continuous development which often is not susceptible to identification because it is generally well compensated by human adaptation on the psychological level. However, at a particular point in life (perhaps because of a lack of adaptation), a significant acceleration of aging symptoms may occur, which result in a clinical picture (or spectrum of symptoms) which was not present until that stage. The age at which senile deterioration appears and its degree of intensity varies widely from individual to individual.

OBS has negative sociological, professional and family effects, as is well known. Moreover, senile deterioration as evidenced by Organic Brain Syndrome, often appears too early, too abruptly and/or too intensely. Under these conditions the individual, rather than progressing through harmonious senility, is subjected to pathological senility with all the undesirable psychological and intellectual consequences.

Hollister, in "Drugs for Mental Disorders of Old Age," J.A.M.A. vol. 234, pp. 195-198, 1975 notes that one sixth of the population over 65 years of age have some manifestations of OBS. One-third of the same group have some type of functional disorder such as depression or neurosis; many have both. Hollister also notes that the characteristic clinical hallmark of this condition is an insidious and progressive loss of memory; that the types of organic lesions formed in the aged brain are the well-known senile plaques and neurofibrillary tangles of Alzheimer; that arteriosclerotic changes are found in only about one-third of the patients displaying OBS in old age; that such changes only contribute substantially to the pathologic conditions in about 10% of the cases; and, finally, that a patient may have severe cerebral arteriosclerosis without much clinical evidence of coronary, renal or peripheral arteriosclerosis, and vice versa. A review of the literature suggests that OBS is not significantly related to the existence of arteriosclerosis or other organic problems of old age.

A typical sequence in the development of organic brain syndrome within an individual may be as follows: there is a diminution in mental alertness and memory that may lead to disorientation and confusion with accompanying personality changes such as increasing irritability, hostility, and emotionality (occasionally to the point of paranoia); finally, motivation and initiative may be completely lost, and an essentially vegetative existence for the individual concerned may be evident. Behavioral disturbances such as poor self-care, unsociability, lack of cooperation and just plain "obstreperousness," and such secondary symptoms such as anxiety, depression, fatigue, dizziness, decreased appetite, and sleep loss may be part of this sequence.

The same and similar symptomatic disorders are discussed in "Senile Dementia: Combined Pharmacologic and Psychologic Treatment," by Yesavage, Westphal and Rush in Journal of the American Geriatrics Society, vol. 29, No. 4, (April 1981).

In order to diagnose and assess the degree of OBS and/or senile dementia (SD) existing in a patient or geriatric population, various standard tests or measurement scales have been developed. Among these may be mentioned the Sandoz Clinical Assessment-Geriatric (SCAG), a behavioral rating scale measuring selected symptoms and signs of dementia; the Hamilton Rating Scale for Depression (HRSD); and the Buschke Selective Reminding Scale (BSRT), a psychometric test of memory and hearing.

The Sandoz Clinical Assessment-Geriatric (SCAG) scale has been described in detail by Shader, Harmatz and Salzman, Journal of the American Geriatric Society, 1974, vol. 22, pp. 107-113, and has been found to be a reliable and valid tool for assessing psychopathology in the elderly.

Clinical assessment of cerebral insufficiency in the elderly requiring a reliable and valid measuring instrument, a rating composed of 17 items has been applied, as described in detail by GEORGES, LALLEMAND, COUSTENOBLE and LORIA, Thérapie (FRANCE), 1977, vol. 32, 2, pp. 173-180, for this purpose. Factor analysis results have shown that the factors identified appeared to well represent the content areas tapped by the rating scale which possesses a construct validity in geriatrics.

Numerous drugs have been suggested for use in the treatment of OBS and SD, many of which are discussed in "A Review of Some Current Drugs Used in the Pharmacotherapy of Organic Brain Syndrome," by Scott in Physiology and Cell Biology of Aging (Aging, vol. 8), edited by Cherkin et al., Raven Press, New York (1979). The ergot aklaloids are the drugs most commonly used world-wide for cognitive disorders; as far as is known, the only such drug clinically available in the United States is dehydroxyergotoxine mesylate (DEM) sold under the trademark "Hydergine."

Yesavage et al. supra. have noted, however, that treatment with ergot alkaloids is quite complicated because of their diverse and undesirable pharmacologic effects.

It is apparent therefore that a need remains in the art for a drug for the treatment of OBS or SD which is safe and reliable and which does not exhibit the complex and disadvantageous pharmacologic effects of DEM.

THE PRIOR ART

The synthesis of therapeutically interesting 5-benzyl-4,5,6,7-tetrahydrothieno [3,2-c] pyridines and certain acid addition salts thereof such as the chlorohydrates and maleates, was described by J. P. Maffrand and F.

Eloy in Eur. J. Med. Chem.—Chimica Therapeutica, September-October 1974-9; No. 5, p. 483-486.

The anti-inflammatory activity and activity in the inhibition of blood-platelet aggregation of certain 5-benzyl-4,5,6,7-tetrahydrothieno [3,2-c] pyridines substituted on the phenyl nucleus was disclosed by M. Podesta, D. Aubert and J. C. Ferrand in Eur. J. Med. Chem.—Chimica Therapeutica, September-October 1974-9; No. 5, p. 487-490.

German Patentschrift No. 24 04 308, issued Feb. 9, 1978, describes a large number of 4,5,6,7-tetrahydrothieno [3,2-c] derivatives and acid addition salts thereof which have anti-inflammatory activity and activity for the inhibition of blood-platelet aggregation.

Castaigne U.S. Pat. No. 4,051,141, issued Sept. 27, 1977 discloses many 5-benzyl-4,5,6,7-tetrahydrothieno [3,2-c] pyridines having various substituents on the benzyl group, and the acid addition salts thereof, primarily the hydrochlorides, which have inhibitor action on blood-platelet aggregation and anti-inflammatory activity. These derivatives are described to exhibit peripheral and cerebral vasodilator action and anti-arrhythmic action.

Amselem U.S. Pat. No. 4,097,482, issued June 27, 1978 describes a class of ortho-substituted 5-benzyl-4,5,6,7-tetrahydrothieno [3,2-c] pyridines and the hydrochloride, fumarate and maleate acid addition salts thereof which are described to have the same combination of inhibitor action against blood-platelet aggregation and anti-inflammatory activity as the other prior art referred to above. These derivatives also exhibit peripheral and cerebral vasodilator action. Derivative No. 7 of this patent, 5-o-cyanobenzyl-4,5,6,7-tetrahydrothieno [3,2-c] pyridine maleate is the closest previously known derivative to the methanesulfonate of the same base used in the present invention.

It is an object of the present invention to provide an effective method of treatment of senile mental deterioration or to delay the onset or increase in severity of the symptoms thereof. Further objects become apparent from the description which follows.

SUMMARY OF THE INVENTION

The present invention is based upon the discovery of the utility of a known drug, 5-o-cyanobenzyl-4,5,6,7-tetrahydrothieno [3,2-c] pyridine methanesulfonate for the alleviation of the symptoms of organic brain syndrome (OBS) and/or of senile dementia (SD). This compound is referred to herein as "MS salt" or generally as "PCR." PCR not only exhibits a valuable and beneficial effect in the control and alleviation of the symptoms of the aged, but especially in controlling or slowing down the onset or development of organic brain syndrome (OBS), especially when such is premature.

The drug may be used in a short course of treatment to temporarily alleviate specific symptoms or in a prolonged or permanent program of maintenance therapy as may be appropriate for the person treated.

The drug may be prepared as described in Amselem U.S. Pat. No. 4,097,482 issued June 27, 1978. The MS salt is also described and claimed in Amselem et al. U.S. patent application Ser. No. 193,906, filed Oct. 6, 1980. The disclosures of the Amselem patent and Amselem et al application are incorporated in full herein by reference. The MS salt when prepared in this way is obtained in 90% yield as white crystals melting instantly at 210° C.

DETAILED DESCRIPTION OF THE INVENTION

The MS salt has very low toxicity and is well tolerated in all useful dosages. Toxicological and pharmacological data on the MS salt are set forth in detail in Amselem et al. U.S. patent application Ser. No. 193,906 filed Oct. 6, 1980, the disclosure of which has been incorporated herein by reference.

More specifically, the invention relates to a geriatric method which comprises administering to an aged person, specially those showing need thereof, a composition which comprises a biologically acceptable carrier and as the active ingredient, PCR, in an effective amount, and alleviating the symptomns of organic brain syndrome of the person. Such symptoms include, without limitation, mental alertness, impairment of recent memory, mood depression, emotional lability, disorientation and fatigue.

The invention also includes compositions for use in geriatric therapy comprising a biologically or pharmaceutically acceptable carrier and PCR in an amount effective to alleviate the symptoms of OBS, and the administration thereof.

CLINICAL TESTING

PCR was tested in accordance with the modified Sandoz Clinical Assessment Geriatric Test (SCAG) which is described in GEORGES, LALLEMAND, COUSTENOBLE and LORIA, THERAPIE (FRANCE), 1977, vol. 32, pp. 173-180, which is incorporated herein by reference.

A double-blind study comparing the PCR with a placebo was conducted with a group of 51 elderly volunteers including 13 men and 38 women. The placebo was exclusively composed by lactose.

The placebo was administered orally to a control group of 25 of the patients, while the other 26 were given PCR in a dosage of 500 mg per day, also administered orally, in two 250 mg dosages given with the noon and evening meals. Whether a patient was given the placebo or PCR was determined by drawing lots. The control group was made by of 6 men and 19 women. The PCR test group was made up of 7 men and 19 women. The sex distribution of the two groups was not statistically significant ($x^2=0.06$). The ages of the patients in the control group ranged from 60 to 89 years. The ages of the patients in the test group ranged from 60 to 82 years.

| Control Group | $m_1 = 74.24 \pm 1.94$ year | |
|---|---|---|
| | | $(+ = .098)$ |
| PCR Group | $m_2 = 72.00 + 1.26$ year | |

In accordance with the modified Sandoz Clinical Assessment-Geriatric (SCAG), as described by Georges et al., supra, the following symptoms were measured as shown in Table I.

SUBJECTS AND TREATMENT

The study was a double-blind study comparing PCR and a placebo.

TABLE I

SCAG Symptom Areas
SCAG Variables
(GEORGES et al)

1. Mental alertness
2. Impairment of recent memory
3. Confusion
4. Anxiety
5. Mood depression
6. Emotional lability
7. Motivation initiative
8. Cooperativeness
9. Sociability
10. Self-care
11. Locomotion
12. Appetite
13. Dizziness
14. Fatigue
15. Headache
16. Sleep
17. Tinnitus

OVERALL RESULTS

The individual results for each patient were taken into account. The overall results give distribution tables of the items which lend themselves to a statistical analysis in accordance with the Kolmogorov-Smirnov method. This analysis can be applied to the limits given by the tables or to the limits of distributions without modification (or corrections) for normal distributions.

The percentage of real significance is then consistently lower to the theoretical percentage for continuous samples. For instance, if a result is significant at the 5% level in accordance with the tables, it can be expressed in the present case as: p=5%.

ITEMIZED RESULTS

The Control Group showed no change in any of the symptoms tested.

The PCR-treated group of patients showed improvements of the following symptoms, as follows after 1 and 2 months of treatment.

|  | ONE MONTH | TWO MONTHS |
| --- | --- | --- |
| Mental Alertness | $p \leq 0.01$ | $p \leq 0.001$ |
| Impairment of Recent Memory | $p \leq 0.007$ | $p \leq 0.004$ |
| Mood Depression | $p \leq 0.03$ | no change |
| Emotional Lability | $p \leq 0.07$ | $p \leq 0.001$ |
| Disorientation | $p \leq 0.001$ | $p \leq 0.001$ |
| Fatigue | $p \leq 0.07$ | $p \leq 0.01$ |

After two months treatment, the control group of patients showed no change. The PCR-treated group of patients showed continued improvement in certain areas and increased improvement in other areas as shown in the table.

Impairment of recent memory shows a most noteworthy significant improvement.

COMPARISON PCR-TREATED PATIENTS AND CONTROL GROUP FOR EACH SYMPTOM AREA

Differences observed after 1 and 2 months of treatment with placebo and PCR have been compared one to the other according to the Mann and Whitney test. Those symptoms which show the most significant amelioration are the following:

| Mental Alertness | $p \leq 0.03$ |
| --- | --- |
| Impairment of Recent Memory |  |
| 1 month | $p \leq 0.01$ |
| 2 months | $p \leq 0.01$ |
| Depression - 2 months | $p \leq 0.09$ |
| Emotional Lability - 2 months | $p \leq 0.04$ |
| Disorientation |  |
| 1 month | $p \leq 0.05$ |
| 2 months | $p \leq 0.01$ |
| Fatigue - 2 months | $p \leq 0.03$ |
| Headaches - 2 months | $p \leq 0.05$ |

TOLERANCE

In the Control Group, stomach and intestinal problems with one patient was serious enough to call for the treatment to be discontinued.

In the PCR-treated group of patients and in the remainder of the Control group, digestive system tolerance was satisfactory. Discomfort was temporary or minor, when observed. No differences were observed between the control and the PCR-treated patient groups in terms of localization of the stomach or intestinal discomfort to the extent felt.

Overall tolerance in other respects was quite satisfactory.

From the data and our work, PCR was found to be a useful drug for geriatric medicine in alleviating and controlling senility symptoms, more particularly organic brain syndromes, which are clinically identifiable by a general psychological depression or decrease in mental alertness and memory.

The preferred dosage for administration is the lowest dosage which shows an improvement or alleviation of the symptoms of senility. Daily dosage may be as small as 10 mg or as high as 800 mg or more where such treatment is called for under the circumstances. Daily dosage of about 500 mg of PCR is quite satisfactory. The daily dosage can be administered in one or more administrations. Treatment can be made for one or two weeks, if so desired, generally at least one month and preferably two months is advisable for alleviation of the symptoms. Generally, aged patients will be placed on PCR-therapy under medical control and therapy will be continued as long as necessary, or discontinued as may be called for under the circumstances and condition of the patients. The drug of the invention is therefore useful in improving the quality of life of the aged.

PCR may be formulated for oral administration as tablets, coated tablets, capsules, drops or syrups with the usual pharmaceutically acceptable carriers, including excipients or adjuvants. As shown above, a preferred dosage unit is a capsule containing about 250 mg of PCR alone or with any desired pharmaceutically acceptable carrier, for administration twice daily, preferably after the mid-day and evening meals.

While the invention has been described above entirely in connection with the presently preferred PCR, it is recognized that the salts of the same base described in Ser. No. 193,906 referred to above, and other salts of that base, including the maleate of Amselem U.S. Pat. No. 4,097,482 and the other derivatives and salts described in that patent; the related thieno [3,2-c] pyridine derivatives of Castaigne U.S. Pat. No. 4,051,141; the thieno [2,3-c] and thieno [3,2-c] derivatives of Maffrand U.S. Pat. No. 4,147,787; and the [3,2-c] derivatives of Blanchard U.S. Pat. No. 4,120,649; may all be considered equivalents of the MS salt to the extent that they share any degree of activity of the type disclosed herein for the MS salt.

We claim:

1. A geriatric method which comprises administering orally to an aged person a composition which comprises a biologically acceptable carrier and as the active ingredient, 5-o-cyanobenzyl-4,5,6,7-tetrahydrothieno [3,2-c] pyridine methanesulfonate, in an effective amount, and alleviating symptoms of organic brain syndrome of that person.

2. The method of claim 1 in which the symptoms which are alleviated are the symptoms of senile deterioration in the symptom areas of the modified Sandoz Clinical Assessment-Geriatric Evaluation.

3. The method of claim 1 in which the symptoms which are alleviated include impairment of recent memory.

4. The method of claim 1 in which the symptom which is alleviated is lack of mental alertness.

5. The method of claim 1 in which the symptom which is alleviated is mood depression.

6. The method of claim 1 in which the symptom which is alleviated is emotional lability.

7. The method of claim 1 in which the symptom which is alleviated is disorientation.

8. The method of claim 1 in which the symptom which is alleviated is fatigue.

9. The method of claim 1 in which the symptoms which are alleviated include the following: mental alertness, impairment of recent memory, mood depression, emotional lability, disorientation and fatigue.

10. The method of claim 1 wherein the daily dosage is about 500 mg.

11. The method of claim 1 wherein the composition is administered for at least 1 month.

12. The method of claim 1 wherein the composition is administered for at least 2 months.

13. A composition for use in geriatric therapy which comprises a pharmaceutically acceptable carrier and, in an effective amount to alleviate the symptoms of organic brain syndrome, 5-o-cyanobenzyl-4,5,6,7-tetrahydrothieno [3,2-c] pyridine methanesulfonate as the active ingredient.

14. A composition for use in geriatric therapy especially suited for oral administration which comprises a pharmaceutically acceptable carrier and, in an effective amount to alleviate at least one of the symptoms of organic brain syndrome, 5-o-cyanobenzyl-4,5,6,7,-tetrahydrothieno [3,2-c] pyridine methanesulfonate as the active ingredient.

15. A geriatric method which comprises administering to an aged person having the symptoms which include at least one of the following: mental alertness, impairment of recent memory, mood depression, emotional liability, disorientation and fatigue, a composition comprising a pharmaceutically acceptable carrier and as the active ingredient, an effective amount of 5-o-cyanobenzyl-4,5,6,7-tetrahydrothieno [3,2-c] pyridine methanesulfonate so as to cause alleviation of at least one of said symptoms.

16. A geriatric method which comprises orally administering to an aged person a composition comprising a pharmaceutically acceptable carrier and 5-o-cyanobenzyl-4,5,6,7-tetrahydrothieno [3,2-c] pyridine methansulfonate in an effective amount to inhibit at least one of the symptoms of organic brain syndrome including mental alertness, impairment of recent memory, mood depression, emotional lability, disorientation and fatigue.

* * * * *